United States Patent [19]

Avery et al.

[11] Patent Number: 4,910,192

[45] Date of Patent: Mar. 20, 1990

[54] TOPICALLY ACTIVE STEROIDAL ANTI-INFLAMMATORY AGENTS

[75] Inventors: Mitchell A. Avery; Masato Tanabe, both of Palo Alto; Dennis Yasuda, Campbell; George Detre, Saratoga, all of Calif.

[73] Assignee: SRI International, Menlo Park, Calif.

[21] Appl. No.: 128,980

[22] Filed: Dec. 4, 1987

[51] Int. Cl.[4] .......................... A61K 31/56; C07J 1/00; C07J 71/00

[52] U.S. Cl. .................................... 514/180; 514/181; 514/182; 260/397.47; 540/62

[58] Field of Search .................... 260/397.47; 514/181, 514/177, 180, 182; 540/62

[56] References Cited

U.S. PATENT DOCUMENTS

| | | | |
|---|---|---|---|
| 2,787,623 | 4/1957 | Bebert | 260/397.47 |
| 3,053,834 | 9/1962 | Fried | 260/397.47 |
| 3,169,978 | 2/1965 | Diassi et al. | 260/397.47 |
| 3,316,282 | 4/1967 | Ivashkiv | 260/397.5 |
| 3,405,127 | 10/1968 | Shaw | 260/397.5 |

OTHER PUBLICATIONS

Taub et al. "Cortical Steroids Substituted at C-12" J Am Chem Soc, vol. 79, 452 (1979).
Remingtons Pharmaceutical Sciences 15th Ed 1975.

*Primary Examiner*—Joseph A. Lipovsky
*Attorney, Agent, or Firm*—Irell & Manella

[57] ABSTRACT

Introduction of a C-12 substituent and especially a β C-12 substituent into glucocorticoids improves their usefulness as topical antiinflammatories by increasing their topical activity relative to their systemic activity, thus reducing systemic side effects such as adrenal suppression.

14 Claims, 4 Drawing Sheets

FIG. I

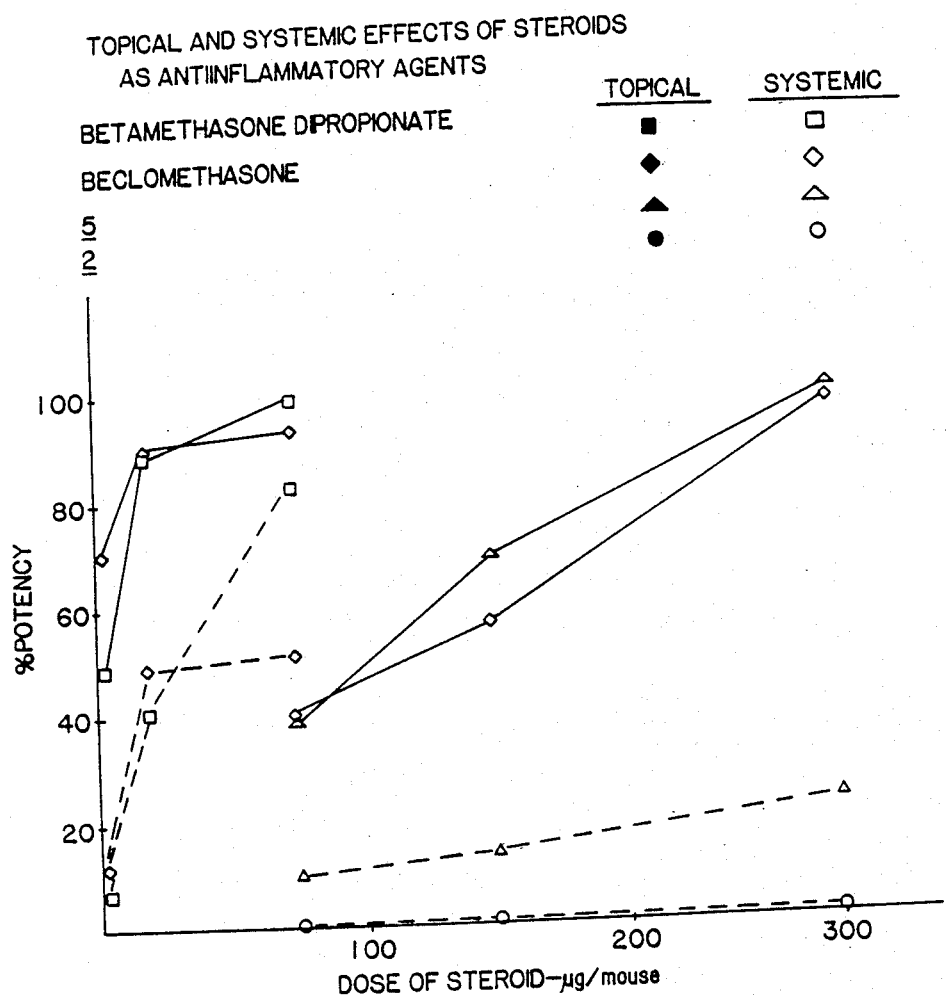

TOPICALLY ACTIVE STEROIDAL ANTI-INFLAMMATORY AGENTS

BACKGROUND OF THE INVENTION

1. Field of the Invention

This invention concerns newly synthesized glucocorticoids and their local use both as topically active anti-inflammatory agents and as inhalant anti-inflammatory agents for the control of asthma.

2. Description of Prior Art

The adrenal glands continuously produce glucocorticoids. These compounds give rise to a range of critical regulatory functions in the body. Over the past thirty years researchers have synthesized a variety of glucocorticoid analogs and have administered these synthetic analogs as well as the natural materials to treat a variety of conditions. For example, they have been administered systemically or locally as aerosol inhalants to treat asthma that does not respond to other forms of treatment; to treat muscle inflammation; and they have been injected into inflamed muscles and connective tissues to reduce local inflammation. In these systemic applications, there is a serious side reaction. That is, as the glucocorticoids are administered, a feedback signal is delivered to the adrenals which shuts down their production of glucocorticoid material. This effect is referred to in the literature as "adrenal suppression". When the administered dose is withdrawn, there is a substantial lag period before the adrenals receive a signal from the brain to begin production anew. The body is left without an adequate supply of glucocorticoids. This can lead to shock, coma and death.

The glucocorticoids have also been used as topical agents. They have been used to treat psoriasis and other proliferative skin diseases, poison oak, poison ivy and like allergenic responses, atopic dermatitis, diaper rash and the like. In these applications, the corticoid is applied as a cream or lotion. With glucocoticoids used heretofore, these topical applications can present the same adrenal suppression difficulties. When large areas of skin are involved in the treatment, or the treatment is continued over long periods of time, the prior materials are absorbed through the skin to levels which can lead to systemic reactions such as adrenal suppression. Similarly, when repeated inhalation doses are desired with prior materials, systemic reactions become an issue and limit the amount of material which can be safely administered.

The present invention provides a family of new glucocorticoids which have excellent topical activity but which do not appear to give rise to systemic side effects on the order of those previously observed. Although not understood with certainty, it is proposed by the inventor herein that this effect is either the result of uniquely superior topical activity or the result of unexpectedly favorable partitioning of topical and systemic activity. Thus, the compounds of this invention are topically useful for dermatological conditions and as inhalants (such as replacements for beclomethasone dipropionate) for the control of asthma.

As will be appreciated, a vast number of steroidal analogs have been disclosed in the literature. A number of these are now commerical products such as prednisone, cortisone, betamethasone, beclomethasone, dexamethasone, the 17,21-dipropionate of the latter three, and the like. The present materials include a beta substituent at the steroid C-12 position. Others have substituted the C-12 position in the past, using different techniques and inserting different substituents from those of the present invention. See, for example, U.S. Pat. No. 4,198,336; U.S. Pat. No. 4,086,254; U.S. Pat. No. 3,934,013; M. J. Green, et al., *J Chem Soc Chem Comm* (1977), 611; D. H. R. Barton, et al., *J Chem Soc* (Perkin 1) (1973), 2365; D. Taub, et al., *J Am Chem Soc*, Vol. 79, 452; E. M. Chamberlin, et al., *J Am Chem Soc*, Vol 79, 456; J. E. Herz, et al., *J Am Chem Soc*, Vol 78, 2017; D. Taub, et al., *J Am Chem Soc*, Vol 78, 2912; P. A. Diassi, et al., *J Am Chem Soc*, Vol 83, 4249; M. Wolff, *Burger's Medicinal Chemistry*, Part III, 4th Ed., Manfred E. Wolff (Wiley-Interscience, 1981), at pp. 1308–09.

STATEMENT OF THE INVENTION

It has now been found that substituting the C-12 of glucocorticoids increases the topical anti-inflammatory activity of the compound relative to their systemic activity. The C-12 substituent can be a hydroxyl, but is preferably a lipophilic group such as lower alkyl or carboxylic acid esters of a C-12 hydroxyl. The substituent can be in the $\alpha$ position but, unexpectedly, $\beta$-substitution is preferred. While the prior art teaches 12$\alpha$ substitution, 12$\beta$ substitution is unknown. See, e.g., M. Wolff, supra.

The invention can be embodied as new glucocorticoid materials having C-12 substituents.

In other embodiments the invention provides methods for producing these new C-12 substituted glucocorticoids.

In yet other aspects the invention provides topical pharmaceutical formulations comprising these C-12 substituted materials and their use as anti-inflammatories. In addition, these materials can be formulated as well as aerosols for the control of asthma.

DETAILED DESCRIPTION OF THE INVENTION

This detailed description has the following sections:
1. Brief Description of the Drawings.
2. The Glucocorticoid Compounds.
3. Methods of Preparation.
4. Pharamaceutical Formulations and their Use.
5. Examples.

1. Brief Description of the Drawings

Figure 1:
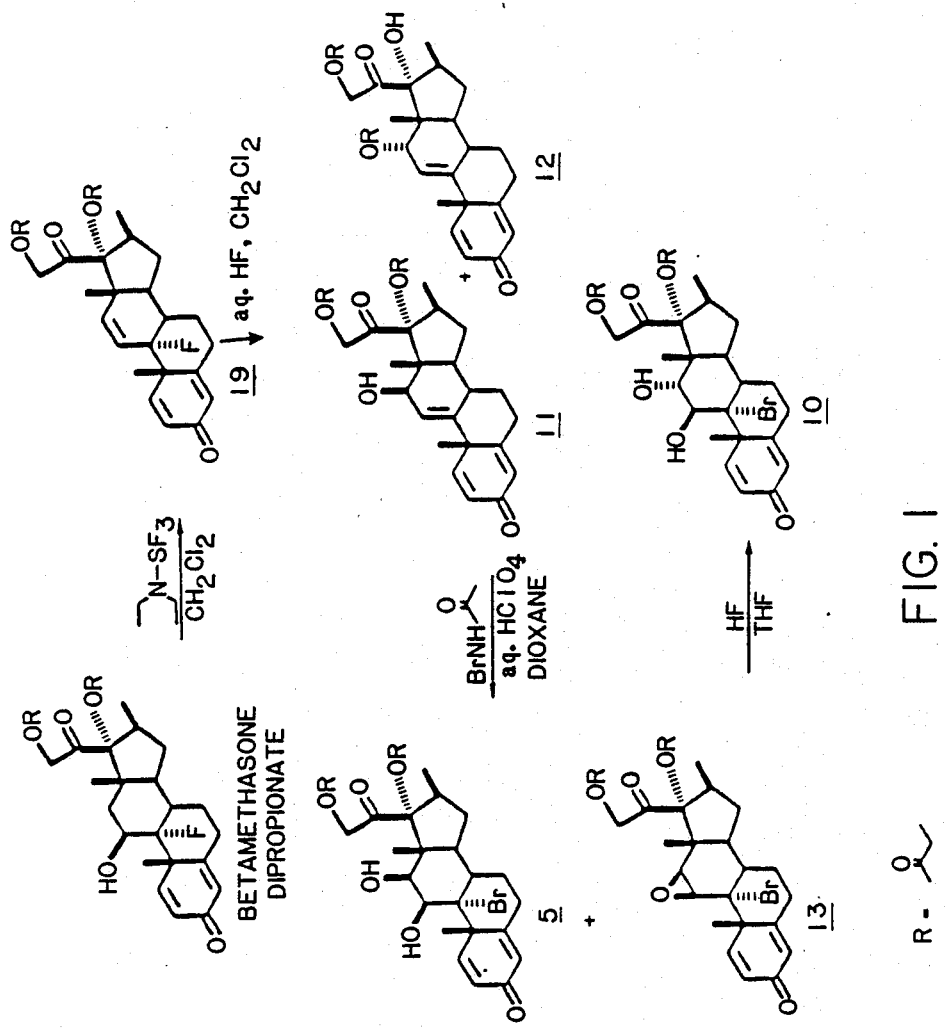
Figure 2:
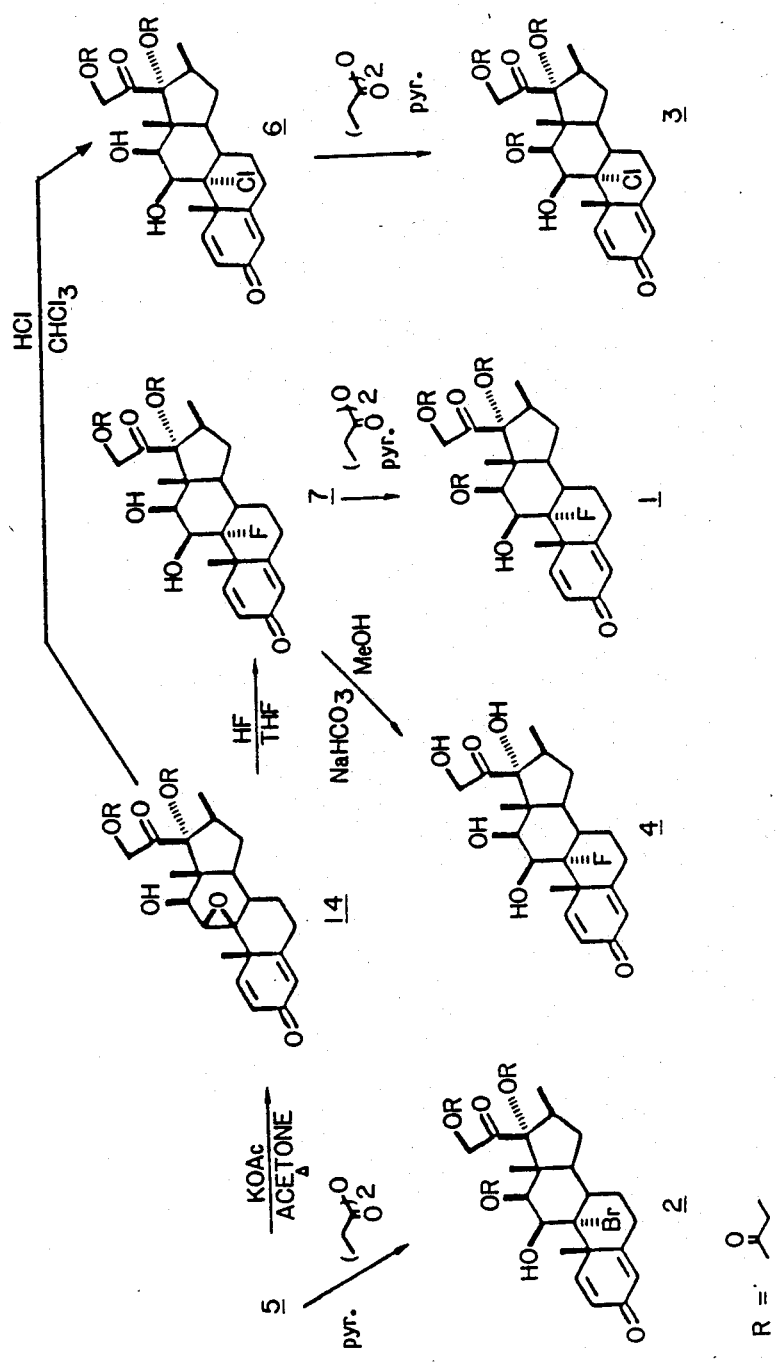
Figure 3:
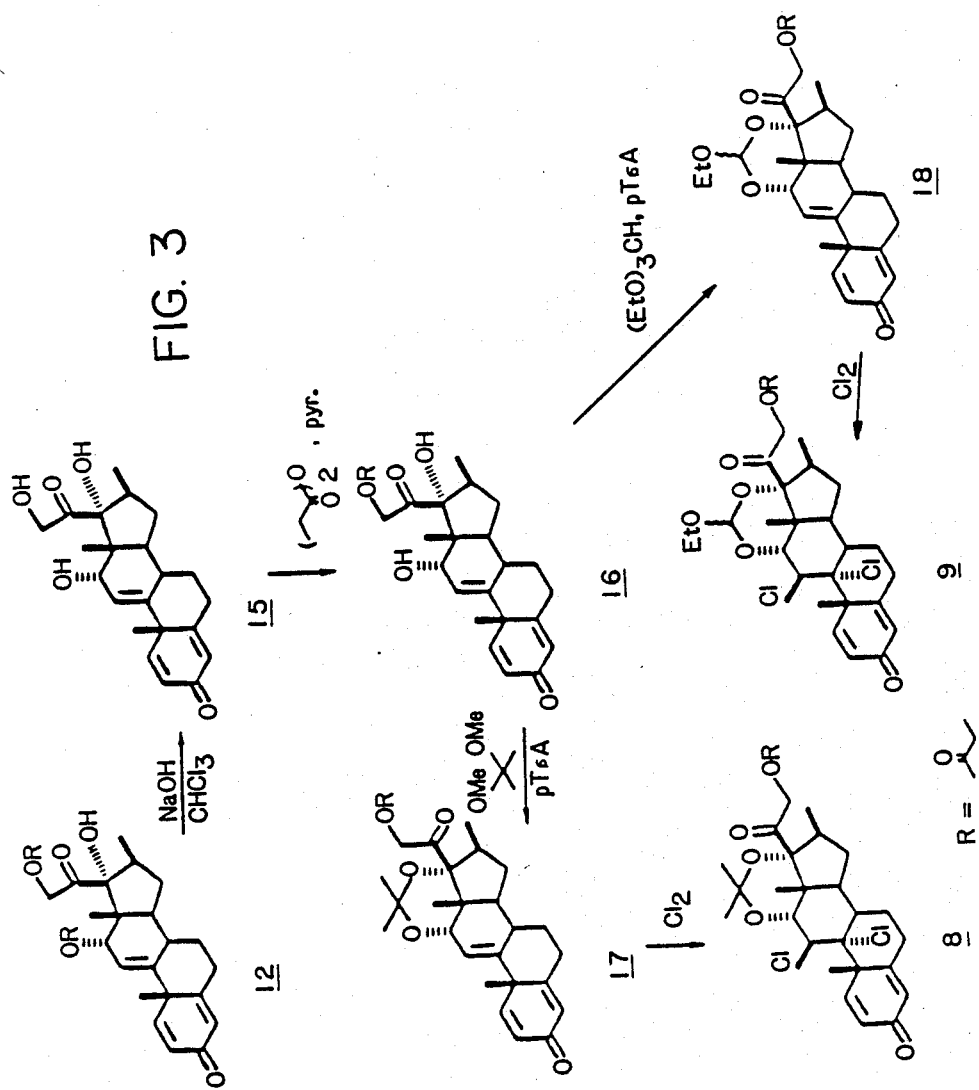

This invention will be described with reference being made to the accompanying drawings in which FIGS. 1 through 3 are schematic chemical formulas illustrating methods for preparing the compounds in accord with this invention.

FIG. 4 is a graph illustrating the topical activity of the compounds of this invention.

2. The Glucocorticoid Compounds

In this description, reference is made to various positions on the glucocorticoid pregnene ring structure. The positional numbering system used herein is shown in Formula I.

Formula I

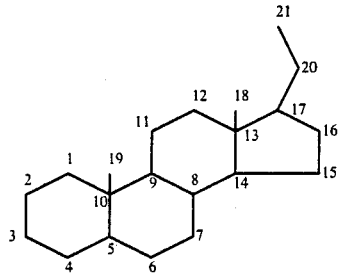

The substituent introduced at the C-12 position can be in the α or β configuration, with the β configuration preferred. The preference is unexpected since virtually 12β corticoids are known or have been tested. And, of C-12 substituted steroids (α or β), the art does not teach or suggest anything about a possible paritioning of topical and systemic effects. In the various structural formulas in the application, the C-12 substituent is often shown as $R^{12}$. This $R^{12}$ is a group covalently bonded to the 12 carbon. It can be selected from a hydroxyl moiety or a lipophilic group attached to the hydroxyl, such as an alkyl- or aryl-substituted ether, an ester, carbonate, carbamate and the like. $R^{12}$ can also be one leg of a bridge linking the 12 and 17 carbons.

Preferred $R^{12}$ groups include lower alkyls, both branched and straight chain ("lower" as used herein means from 1 to 10 carbon atoms and preferably 1 to 4 carbon atoms), such as methyl, ethyl, propyl, nonyl and decyl, and especially methyl or ethyl; hydroxyl or lower carboxylic acid esters of this hydroxyl; and particularly a 1 to 4 carbon carboxylic acid ester and one leg of a

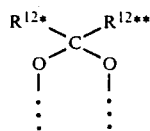

bridge between the 12 and 17 carbons wherein $R^{12*}$ and $R^{12**}$ are hydrogen or lower alkyls, especially methyls.

The $R^{12}$ substituent can be used with advantage with the natural glucocorticoid materials such as cortisone and hydrocortisone, i.e.,

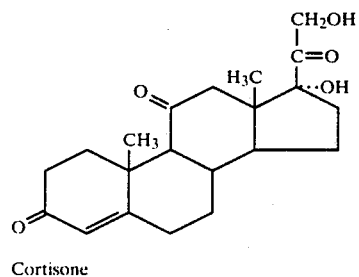

Cortisone

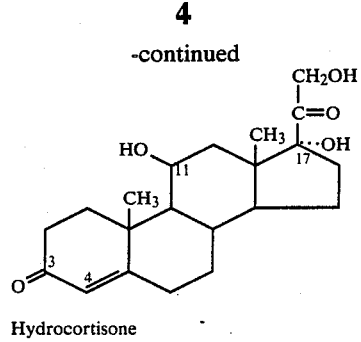

Hydrocortisone

The $R^{12}$ substituent offers its advantages when used in combination with other known modifications to these materials as well. These modifications are summarized by Lewis H. Sarett, Arthur A. Patchett, and Sandford L. Steelman in their review article "The Effects of Structural Alteration on the Anti-inflammatory Properties of Hydrocortisone" appearing at pages 11–153 of Fortschr. Arzneimittel-forsch., Vol. 5 (1963). Other modifications are set out in M. Wolff, supra Chapter 63 (pages 1273–1316) which is incorporated by reference. These references and the references they include are incorporated herein by reference for brevity.

These modifications are illustrated by general Formula II. The material of Formula II contain a range of "R" substituents. $R^{12}$ has already been described. The other R's such as $R^2$, $R^4$, $R^6$, $R^9$, etc., in each case include the natural substituent as well as the modifications which are as described below.

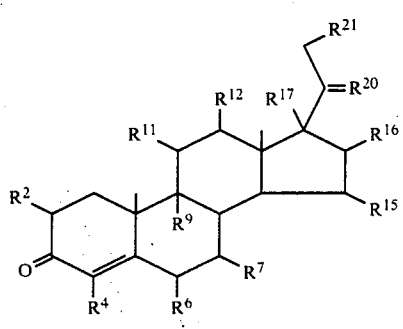

Formula II

Representative structural modifications which can be beneficial to activity include introducing an olefinic bond between the 1 and 2 carbons. This can increase activity 3-4 fold. Removal of the 19-methyl group and aromatization of ring "A" is also a known modification. Such a modification does not affect activity. Expansion of the "D" ring to a 6-membered ring gives D-homocortisone acetate, a compound whose activity is slightly decreased. Other structurally modified glucocorticoids which can benefit from the present C-12 addition by M. Wolff at page 1304 include the following materials disclosed:

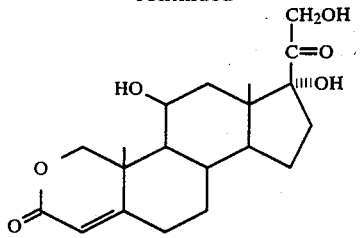

Another point of modification is the 2-carbon. The 2-carbon can include an $R^2$ unit which can be hydrogen or can be a lower alkyl for increased activity.

While almost all active anti-inflammatory steroids have a carbonyl group at the 3 position, there are some exceptions. As noted above, the "A" ring may be aromatic, in which case the 3-carbon is substituted with a hydroxyl group. Another mode of substitution which provides compounds of substantially increased anti-inflammatory activity is the inclusion of a pyrazole ring adjacent to the "A" ring, e.g., the 2'-phenylpregn-4-ene [3,2-C] pyrazoles and 2'-[p-fluorophenyl]pregn-4-ene [3,2-C] pyrazoles and 2'-[p-fluorophenyl]pregn-4-ene [3,2-C] pyrazoles of corticoids.

At the 4 position, it is generally preferred that the $\Delta^4$ bond be retained, as reduction of the double bond results in a many-fold decrease in anti-inflammatory activity. While the C-4 may be substituted, e.g., with a lower alkyl or a halogen substituent, it is preferred that there be no substitution at this position.

The 6 position can be substituted with a halogen, e.g., fluoro or with an $\alpha$ or $\beta$ halo. "Halo" is used to include fluoro, chloro, bromo or the like, especially a fluoro or chloro. The 6 position can also be a lower alkyl in the $\alpha$ position. This 6 group is referred to as $R^6$.

The 6 and 7 positions can be substituted with an $R^6/R^7$ bridging group such as an acetonide between the 6$\alpha$/7$\alpha$.

A double bond may also be introduced between the 6 and 7 positions, although such a modification generally has little effect on anti-inflammatory activity.

The 7 position may be either $\alpha$- or $\beta$-substituted with, e.g., a lower alkyl, e.g., methyl, methylthio, a halo or a thio such as ethylthio, acetylthio, or thiocyano moiety. Such substituted compounds, in general, have reduced anti-inflammatory activity. Some 6,7-disubstituted compounds are active, such as the 6,7-difluoro derivative and the 6$\alpha$,7$\alpha$-difluoromethylene compound.

An important substitution is the 9$\alpha$ position where the hydrogen can be replaced with a halo—particularly a fluoro or chloro substituent.

The 11 position hydroxyl can be replaced by hydrogen or a $\beta$ halo or it can be oxidized to a carbonyl.

The 15 position can be substituted with a lower alkyl, preferably an methyl, or with a halo, preferably a fluoro, substituent.

A 16 position hydrogen can be replaced to achieve increased activity. Representative substitutions include an $\alpha$ hydroxy, an $\alpha$ or $\beta$ lower alkyl or halo.

The 16 and 17 positions can be bridged with an $R^{16}/R^{17}$ bridging group such as an acetonide or an acetal.

The 17-position may be substituted with lower alkyl or halo without substantial loss in anti-inflammatory activity.

The 20 position can be reduced to replace the $R^{20}$ carbonyl with an OH or with two hydrogens or it may be ketalized. The 21 position oxygen can be removed or an alkyl or halo can be added, again, without substantial reduction in anti-inflammatory activity.

These substitutions can be effected using the art-taught methods disclosed in the incorporated review and text and the references cited therein which also are incorporated by reference.

It is important to note that the $R^{12}$ substituents of this invention and the chemistry used to insert them are compatible with these known modifications such that by using appropriate protection groups and the like, the conventional methods for adding the other groups can be used.

Out of these substitution patterns several combinations emerge as preferred. For example the 9-halo and especially 9-fluoro or chloro materials and the 16$\alpha$ and $\beta$ alkyl or bridged materials are preferred. Several particular structures which advantageously employ the $R^{12}$ substituents of this invention include:

Hydrocortisone (4-pregnene-17$\alpha$, 11$\beta$, 21-triol-3,20-dione)
Cortisone (4-pregnene-17$\alpha$, 21-diol-3,11,20 trione)
Cortisol
Cortisol-17-butyrate
Cortisol-17-valerate
Prednisolone (1,4-pregnadiene-11$\beta$,17$\alpha$,21-triol-3, 20 dione)
Prednisolone 21-acetate
Prednisolone 21-valerate
Prednisone (1,4-pregnadiene-17$\alpha$,21-diol-3,11,20 trione)
Triamcinolone (9$\alpha$-fluoro-16$\alpha$ hydroxy prednisolone)
Dexamethasone (9$\alpha$-fluoro-16$\alpha$ methyl prednisolone)
Dexamethasone 21-acetate
Dexamethasone 21-phosphate
9$\alpha$-Fluoro-hydrocortisone
Triamcinolone
Triamcinolone acetonide
6$\alpha$-Fluoro-triamcinoloneacetonide
Flurandrenolone
Flurandenolide
Fluocinolone
Fluocinolinide
Fluocinolone acetonide
Fluoroprednisolone
Fluoromethalone
Dichlorisone
Betamethasone
Betamethasone 21-acetate
Betamethasone 17-valerate
Betamethasone dipropionate
The bromo analogs of betamethasone dipropionate
Beclomethasone
Beclomethasone dipropionate
Mometasone furoate
Fluoromethalone
Desonide
Halcinonide
Budesonide Most preferred materials are those shown in the Examples as compounds 1, 2, 3, 4, 5, 6, 7, 8, 9, 10, i.e.,

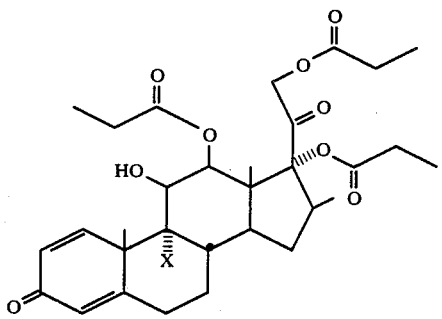

1 X = F
2 X = Br
3 X = Cl

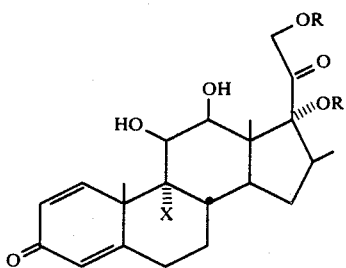

4 R = H, X = F

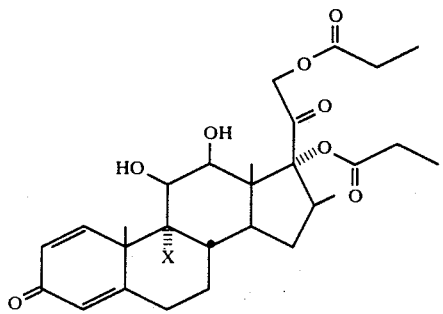

5, X = Br
6, X = Cl
7, X = F

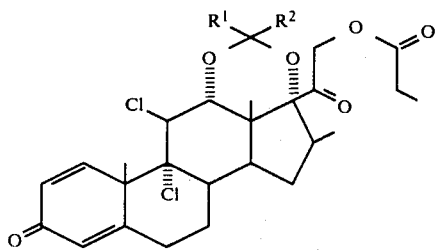

8 R¹ = Me, R² = Me
9 R¹ = H, R² = OCH₂CH₃

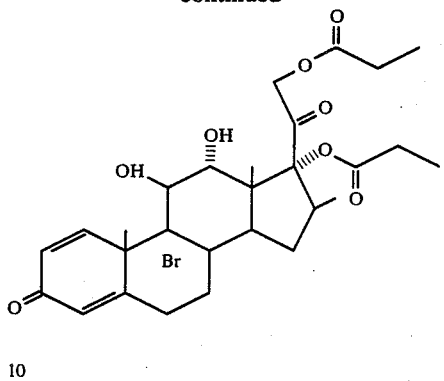

10

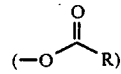

10 and the other lower alkyl and halo equivalents thereof.

3. Methods of Preparation

The $R^{12}$-substituents can be introduced into the glucocorticoids by the general process of (1) introducing unsaturation at the 11–12 position by dehydration of the appropriate 9,11-fluorohydrin-containing precursors (such as betamethasone dipropionate) with diethylaminosulfurtrifluoride, and (2) solvolysis of the allylic fluoride 10 with acid to introduce an α-alkoxyl $$(-O \overset{O}{\underset{\|}{C}} R)$$

or β-hydroxyl (—OH) at the 12 position and moving the unsaturation to the 9–11 position (compounds 11 and 12, respectively).

At this point the process diverges depending upon the exact 12 position substituent desired.

In the case where a β-OH is desired at 12, hypobromination can be used to give the 11β,12β-oxo 9α-bromo analog as a minor component 13 together with the 11β,12β-dihydroxy-9α-bromo steroid as the major component 5. Upon dehydrobromination of 5, the epoxide 14 is formed which on reaction with HF or HCl affords the 11β,12β-hydroxy-9α-fluoro and 11β,12β-dihydroxy-9α-chloro steroids 7 and 6 respectively.

In the case where an α-OCOR is desired at the 12 position, this can be accomplished during the solvolysis of the $\Delta^{11,12}$,-9α-fluorosteroid 19 which affords 12 as a minor product.

When a bridged group is desired at the 12 position, the C-12 α-OCOR material 12 serves as an intermediate. After hydrolysis and acetylation of 12, the product 16 is then reacted with dialkoxy (dimethoxy) or trialkoxy (trimethoxy) alkyl materials such as 2,2-dimethoxypropane or ethylorthoformate in the presence of acid to introduce the bridge between the 12 and 17 carbons.

4. Pharmaceutical Formulations and Their Use

The present C-12 position substituted materials offer attractive high topical anti-inflammatory activity. They are employed as topically acceptable formulations such as dermatological formulations in solution, suspension, lotion, salve, spray, or cream forms. In these formulations, the glucocorticoid is dissolved, dispersed or suspended in a carrier.

Carriers can be selected widely from materials known to the art for this purpose. For solutions or suspensions, purified water, or mixtures of water with a pharmaceutically acceptable alcohol (e.g., methanol, ehtanol or isopropanol) or the like can be used; creams, salves or lotions can include glycerine, carboxymethylcellulose, acacia, agar, carrageenan, methylcellulose, sorbiton esters or like thickeners or suspending agents and waxes, pharmaceutically acceptable oils, such as white wax, white petroleum, yellow wax, oleic acid, lanolin, cetyl alcohol, cold cream, glycol ethers and the like.

For treatment of asthma, the agents are administered by inhalation using oral or nasal routes. In these applications, the active glucocorticoid can be delivered as a microcrystalline powder in a gaseous vehicle. In the past, various gaseous halohydrocarbons or halocarbons have been favored as inhalent vehicles—for example, trichlorofluoromethane or dichlorodifluoromethane or the like with the active agent presented in a pressure canister having a metering valve. Other vehicles such as air (either compressed or an air flow generated by a fan or by patient action or the like), hydrocarbons, lower ethers, and the like can be used. Solutions in suitable carriers such as water or the like can be used as well.

These and other pharmaceutical necessities and their use in preparing suitable solutions or suspensions and aerosols and the like are described in detail in *Remington's Pharmaceutical Science's 17th Edition*, 1985 (Mack Publishing Co., Easton, PA) chapters 68, 84, and 93 which are incorporated herein by reference.

The C-12 substituted glucocorticoids are administered in a "topically effective amount." This is defined to be an amount effective to produce a desired topical response in a mammalian patient to which the material is topically administered.

Generally this is achieved in dermatological settings by using a dosage form capable of delivering at least about 1-5 mg of active glucocorticoid per about 50 cm$^2$ of skin surface treated. For the control of asthma, a typical dosage is at least about 40 mg per day. It will be appreciated that the dose and dosing pattern actually administered will vary depending upon the condition and patient being treated. An advantage of the present materials is that they permit larger or more frequent dosing with less likelihood of adverse systemic reactions. Thus, larger skin areas can be treated or more frequent inhalation doses can be taken. For example, with many salves now in widespread use, an upper limit of 5 mg or 50 cm$^2$ of skin surface is called for or with aerosols about 1 mg is a maximum daily dose (generally administered in about 0.040 mg bursts). With the present materials, these maxima may be exceeded, sometimes ten-fold or even more. Thus, typical dermatological treatments can employ up to 100 mg of material or more on areas of up to 500 or 1000 cm$^2$ or larger and inhalation can deliver up to 10 or 20 mg per day.

The present invention will be further illustrated by the following Examples. These are presented to illustrate the invention and are not to be construed as limiting its scope. In these Examples reference is made to the reaction scheme set forth in the first three figures. The numbers in the Examples which identify compounds are the same numbers used in these Figures. The graph shown in FIG. 4 is also referenced.

EXAMPLES

I. Chemical Procedures

Solvolysis of 17α,21-dihydroxy-9α-fluoro-16β-methyl-preg-1,4, 11-triene-3,20-dione dipropionate (10). To a solution of the vinyl fluoride 19 (1 g or 0.00206 mol) in CH$_2$Cl$_2$ was added 48% aqeous HF (0.25 ml). The heterogeneous mixture was stirred rapidly at room temperature for 4 hours and then was diluted with CH$_2$Cl$_2$ (100 ml). The resulting mixture was washed 3×100 ml H$_2$O, filtered, and the solvent removed to give 942 mg of residue. The three major products were isolated by PTLC using ether-benzene (1:3). The least polar compound was 16β-methyl-3,17α,21-trihydroxy-9,10-seco-preg-1,3,5,11-tetraene-9,20-dione 17-21-dipropionate, obtained in 10% yield. IR (nujol): 3350, 1740, 1670 cm$^{-1}$. UV (MeOH): λ 222 nm (ε16,900), 282 (2,400). The next polar compound was 16β-methyl-12α,17α,21-trihydroxypreg-1,4,9-triene-3,20-dione 12,21-dipropionate 12, obtained in 10% yield, m.p. 135°–136° C. IR (nujol): 3420, 1740, 1670 cm$^{-1}$. The most polar compound was 16β-methyl-12β,17α,21-trihydroxy-preg-1,4,9-triene-3,20-dione 17,21-dipropionate 11, obtained in 40% yield, m.p. 77°–80° C. IR (nujol): 3400,1740,1670 cm$^{-1}$.

Hypobromination of the allylic alcohol (11). To a solution of the allylic alcohol 11 (320 mg or 0.661 mmol) in dioxane (20 ml) at room temperature under argon was added recrystallized N-bromoacetamide (300 mg or 2.17 mmol) followed by aqeous HClO$_4$ (0.5N, 0.3 ml). The flask was wrapped in foil, the mixture stirred 22 hours, poured into 5% aqeous Na$_2$SO$_3$, and extracted 3×EtOAc. The combined organic layer was washed 2×5% aqueous Na$_2$SO$_3$, 1×H$_2$O, dried over anhydrous MgSO$_4$, filtered, and the solvent removed. The residue was purified by PTLC (1:1 EtOAc-hexane) to give 9α-bromo-17α,21-dihydroxy-11β,12β-oxo-16β-methylpregna-1,4-dien-3,20-dione 17,21-dipropionate 13 (55 mg or 15% yield) as the least polar product. The more polar compound was 9α-bromo-17α,21-dihydroxy-11β,12β,17α,21-tetrahydroxypregna-1,4-dien-3,20-dione 17-21-dipropionate 5 (283 mg or 63% yield).

9α-bromo-16β-methyl-21,17α,12α,11β-tetrahydroxypregna-1,4-diene-3,20-dione 17,21-dipriopionate ester (10). To a solution of 2:1 THF/HF (10 ml) in a stoppered teflon vessel was added the epoxide 13 (160 mg). After 36 hours at 5° C. followed by 13 hours at room temperature, the mixture was poured into aqeous NaHCO$_3$ (sat., 150 ml). The mixture was extracted with ether (3×50 ml), dried over MgSO$_4$, filtered, and the solvent evaporated. The residue was chromatographed on one PTLC plate (2 mm, silica gel) with 1:1 Et$_2$O-benzene to give 10, 150 mg or 90.9% yield.

9β,11β-epoxy-16β,17α,21-trihydroxy-pregna-1,4-diene-3,20-dione 17,21-dipropionate (14). To a solution of the bromohydrin 5 (1.5 g or 2.58 mmol) in dry acetone (60 ml) was added anhydrous KOAc (2.0 g or 0.02 mmol). The mixture was refluxed under argon for 20 hours, cooled, poured into H$_2$O, and extracted 3×35 EtOAc. The combined organic layer was washed in 2×50 ml H$_2$O, dried over MgSO$_4$, filtered, and the solvent evaporated. The residue was recrystallized from Et$_2$O/hexane to give 14 (840 mg or 65% yield), m.p. 239°–241° C.

9α-fluoro-16β-methyl-11β,12β,17α,21-tetrahydroxy-pregna-1,4-diene-3,20-dione 17,21-dipropionate (7). A solution of anhydrous HF (3 ml) in dry THF (4 ml) in a teflon vessel at 5° C. was treated with the epoxide 14 (100 mg or 0.2 mmol). The mixture was stored at 5° C. for 24 hours and then poured into a stirred suspension of NaHCO$_3$ (15 g) in EtOAc (100 ml). After 1 hour, the mixture was filtered and the solvent evaporated. The residue was chromatographed on one PTLC plate (2 mm, silica gel) with Et$_2$O-benzene (7:3) to give 7 (88 mg or 84.6% yield), which could be crystallized from Et$_2$O-hexane, m.p. 119°–121° C. IR (nujol): 3430, 1730, 1660, 1610, 1375, 1180 cm$^{-1}$.

9α-fluoro-16β-methyl-21,17α,12β,11β-tetrahydroxypregna-1,4-diene-3,20-dione 21,17,12-tripropionate ester (1). To a solution of the diol 7 (6.6 mg) in CH$_2$Cl$_2$ (0.25 ml) was added propionic anhydride (10 μl), pyridine (15 μl), and 4-N,N'-dimethylaminopyridine (1 mg). After 30 minutes, the reaction mixture was applied to one PTLC plate (1500 micron, silica gel) and eluted with 30:70 benzene-ether. The product 1 (7 mg or 96% yield) was obtained as a white powder.

9α-bromo-16β-methyl-21,17α,12β, 11β-tetrahydroxypregna-1,4-diene-3,20-dione 21,17,12-tripropionate ester (2). The procedure for the preparation of 1 from 7 was followed using 5 to give 2 in 73% yield.

9α-fluoro-16β-methyl-21,17α,12β,11β-tetrahydroxypregna-1,4-diene-3,20-dione 21,17,12-triproprionate ester (4). To a solution of 7 (30 mg or 0.058 mmol) in methanol (3 ml) under argon was added NaHCO$_3$ (200 mg). The mixture was refluxed 4 hours, poured into EtOAc (30 ml), and washed 3×H$_2$O (10 ml). The organic phase was dried over MgSO$_4$, filtered, and the solvent removed. The residue was purified on one PTLC plate (1500 micron, silica gel), eluting with EtOAc to give the product 4 (18 mg or 76% yield).

16β-methyl-12α,17α,21-trihydroxy-preg-1,4,9(11)-triene-3,20-dione (15). To a solution of 12 (425 mg) in degassed CH$_3$OH/CH$_3$Cl$_3$ (1:1, 40 ml) under N$_2$ at 5° C. was added 0.5M NaOH (5 ml). After 3.5 hours at 5° C., the mixture was poured into H$_2$O (100 ml) and extracted 3×EtOAc (50 ml). The combined organic layers were dried over MgSO$_4$, filtered, and the solvent removed. Chromatography on two PTLC plates (2000 micron, silica gel) with 80% EtOAc/hexane gave 15 (223 mg or 69% yield) as a white foam.

16β-methyl-21,17α,12α-trihydroxypregna-1,4,9(11)-triene-3,2-dione (16). To a solution of the triol 15 (150 mg) in dry pyridine (5 ml) was added propionic anhydride (0.04 ml) at 20° C. After 3 hours, an additional portion of anhydride was added (0.02 ml) at 20° C. The mixture was stirred overnight at room temperature, the solvent was evaporated, and the residue placed on one PTLC plate (2 mm, silica gel) and eluted with 1:1 EtOAc/hexane. The triol 15 (38 mg) was recovered. The product 16 (113 mg or 80% yield) was obtained as white powder.

16β-methyl-21,17α,12α-trihydroxypregna-1,4,9(11)-triene-3,2-dione 21-propionate ester; 17,21-acetonide (17). To a solution of the diol 16 (85 mg) in 6 ml dry THF was added 2,2-dimethoxypropane (1 ml) and p-toluenesulfonic acid (2 mg). The mixture was refluxed under N$_2$ until 16 was not detected by TLC (ca. 6 hours). Solid NaHCO$_3$ was then added (100 mg) and the mixture stirred 30 minutes, filtered, and the solvent removed. Chromatography on one PTLC plate with 4:6 EtOAc-hexane gave 17 (77 mg or 83% yield) as a white foam.

11β,9α-dichloro-16β-methyl-21,17α,12α-trihydroxypregna-1,4, diene-3,20-dione 21-propionate ester; 12,17-acetonide (8). The acetonide 17 (100 mg) was dissolved in a solution of CHCl$_3$ (5 ml) and pyridine (0.5 ml). Chlorine gas was bubbled through the stirred solution for 30 seconds at room temperature, and then the reaction was stirred 30 minutes. EtOAc was added (50 ml) and the mixture washed 3×25 ml 5% aq. Na$_2$S$_2$O$_3$, 2×25 ml saturated aqeous CuSO$_4$, and 1×saturated aqeous NaCl. The organic layer was dried over MgSO$_4$, filtered, and the solvent evaporated. The residue was chromatographed on one PTLC plate (2 mm, silica gel) with 6:4 EtOAc-hexane to give 8 (56 mg or 49% yield) as a white powder, m.p. 92°–95° C.

16β-methyl-21,17α,12α-trihydroxypregna-1,4,9(11)-triene-3,2-dione 21-propionate ester: 12,17 cyclic ethylorthoformate (18). To a solution of the diol 16 (180 mg) in dry benzene (12 ml) was added ethyl orthoformate (2 ml) and p-toluenesulfonic acid (2 mg). The solution was refluxed and water removed azeotropically for 30 minutes. The mixture was cooled and the solvent removed. The residue was chromatographed on one PTLC plate (2 mm silica gel). The product 18 (as determined by NMR and TLC) was isolated as a mixture of isomers on the orthoformate portion of the molecule (175 mg or 86% yield).

11β,9α-dichloro-16β-methyl-21,17α,12α-trihydroxypregna-1,4-diene-3,20-dione 21 proprionate ester; 12,17 cyclic ethylorthoformate (9). The orthoformate 18 (80 mg) was chlorinated exactly as was the acetonide 17. Purification of the crude product on one PTLC plate with 1:1 EtOAc/hexane (2 mm, silica gel) gave 9 (54 mg or 59% yield) as a mixture of isomers, m.p. 102°–104° C.

9α-chloro-16β-methyl-11β,12β,17α,21-tetrahydroxypregna-1,4-diene-3,20-dione 17,21-dipropionate (6). To a solution of 9β,11β-epoxy-16β-methyl-12β,17α,21-trihydroxy-pregna-1,4-diene-3,20-dione 17,21-dipropionate, 14, (760 mg in 35 ml of chloroform) was bubbled anhydrous hydrogen chloride gas (15 minutes) with stirring. The reaction flask was stoppered and stirring was continued for 10 minutes. Anhydrous hydrogen chloride gas was again bubbled through for 5 minutes, then stirring was continued for 50 minutes. The solvent and the hydrogen chloride was removed under vacuum to yield 735 mg of crude 6 (90% yield). Chromatography on a medium pressure silica gel column (30% ethyl acetate - chloroform) afforded the analytical sample which was crystallized from CH$_2$Cl$_2$—Et$_2$O (m.p. 207°–208° C.). NMR (CDCl$_3$): δ0.99 (s, 3H), 1.16 (t,J=7.7 Hz$_3$,6H), 1.27 (d. J=7.4 Hz, 3H), 1.65 (3s, 3H), 2.42 (m. 4M), 3.1 (br, 1H, exchangeable), 3.65 (br, 1H, exchangeable), 4.35 (d, J=3.6 Hz, 1H), 4.49 (d, J=16.7 Hz, 1H), 4.57 (d, J=3.9 Hz, 1H), 5.34 (d, J=16.3 Hz, 1H), 6.09 (t, J=1.7 Hz, 1H), 6.32 (dd, J=10 Hz, 1.8 Hz 1H), 7.17 (d, J=10 Hz). IR (nujol): 3430, 1730, 1660, 1610, 1380, 1190 cm$^{-1}$. Mass Spectrum: m/e 536 (M+), 449, 421, 347, 329, 311. Exact mass: calc. for C$_{28}$H$_{37}$O$_8$ $^{35}$Cl:536.218; found 536.218.

9α-chloro-16β-methyl-11β,12β,17α,21-tetrahydroxypregna-1,4-diene-3,20-dione 12,17,21-tripropionate. To a solution of the diol 6 (460 mg) in CH$_2$Cl$_2$ (25 ml) was added 0.50 ml of propionic anhydride, 0.59 ml pyridine and 58 mg of 4,4-dimethylaminopryridine. The solution was stirred at room temperature for 4 hours, diluted with methylene chloride, and was then washed with dilute HCl followed by saline water. The organic layer was dried over sodium sulfate, filtered, and evaporated to dryness at reduced pressure. The product (7) was obtained as a gummy solid that was purified by chromatography on a medium pressure silica gel column. The product eluted with benzene-ether (30:70). Crystallization from ether gave an analytical sample m.p. 143°–144° C. NMR (CDCl$_3$): δ1.08 (s, 3H), 1.12 (2, J=7.5 Hz, 3H) 1.15 (t, J=7.3 Hz 6H), 1.62 (s, 3H), 2.41 (m, 6H), 4.51 (dd, J=3.5 Hz, J=0.7 Hz 1H), 4.55 (d, J=16.4 Hz, 1H), 4.63 (d, J=16.4 Hz, 1H), 5.92 (d, J=3.8 Hz, 1H), 6.08 (t, J=1.7 Hz, 1H), 6.30 (dd, J=10 Hz, J=1.8 Hz, 1H), 7.08 (d, J=10 Hz, 1H). IR (nujol):

3420, 1760, 1680, 1390, 1190 cm$^{-1}$. Mass Spectrum: m/e 593 (M+H$^+$), 505, 421, 329, 311. Exact Mass: calc. for $C_{31}H_{41}O_9$ $^{35}Cl$: 592.244; found 592.244.

II. Biological Procedure

The potency of synthetic steroids as anti-inflammatory agents was determined using the mouse croton oil ear test described by B. N. Lutsky, et al. *Drug Research*, 29 (II), 992 (1979). In general, groups of 6-10 female Swiss Webster mice weighing 28-30 g were used for the assay. For each test compound, various amounts were dissolved in acetone containing 850 μM of 12-O-tetradecanoyl-phorbol-13-acetate (TPA). Aliquots of 10 μl from each test solution were carefully applied to the inner aspect of both pinnae of the mice. Five hours after the application, mice were killed, 6 mm punch biopsies from both ears were removed and weighed. Positive and negative control groups were carried out with each test group. The positive group received 10 μl of 850 μm TPA in acetone, and the negative group received 10 μl of acetone alone. The topical potency of a test compound was determined by comparing the net weight increase of the ear biopsies in a test group with that in the positive control group. For determination of the systemic effect, 10 μl of each test solution was applied to the right ear of each test animal; the left, contralateral ear received 10 μl of 850 μM TPA. Five hours later, the animals were killed and ear biopsies were obtained as described above. The systemic potency was determined by comparing the net weight increase of the left ear biopsy with that in the positive control group. To evaluate the separation of topical from systemic effects of a test compound, a therapeutic index was derived by dividing the topical potency (right ear) by the systemic potency (left ear), where a higher index number indicates a greater separation of topical from systemic effects. For all test compounds, betamethasone dipropionate was used as a standard.

III. Biological Results

The compounds 1 through 5 and 7 through 10 were tested in vivo in mice using the Croton Oil Ear Test. Betamethasone dipropionate was used as the standard. The compounds were tested for topical and systemic effects. Dose titration on many of the compounds (Tables 1 and 2) show that no increase in systemic effects are observed as the dose is increased while the topical effect increases. This demonstrates that these compounds are essentially devoid of systemic activity. Also noteworthy is a comparison of the 12β-hydroxy compounds such as 5, 6, and 7 versus the analogous lipophylic esters 1, 2, and 3. For example, a rise in systemic effect with increasing dose for the 12β-hydroxy compounds is more clearly seen when represented graphically (FIG. 4) and is in sharp contrast to the corresponding 12β-esters which show no systemic effect with increasing dose.

TABLE 1

| Compound | Dose | Topical Effect (%) | Systemic Effect (%) |
|---|---|---|---|
| 1 | 3.75 mg/ml* | 16 | 0 |
| 2 | 3.75 mg/ml* | 37 | 4 |

TABLE 1-continued

| Compound | Dose | Topical Effect (%) | Systemic Effect (%) |
|---|---|---|---|
|  | 7.5 mg/ml* | 43 | 5 |
|  | 15 mg/ml* | 69 | 1 |
| 4 | 3.75 mg/ml* | 23 | 5 |
|  | 7.5 mg/ml* | 30 | 3 |
|  | 15 mg/ml* | 75 | 4 |
| 7 | 0.37 mg/ml* | 21 | 13 |
| 5 | 0.37 mg/ml* | 29 | 21 |
| 8 | 3.75 mg/ml* | 12 | 0 |
|  | 7.5 mg/ml* | 32 | 0 |
|  | 15 mg/ml* | 57 | 2 |
| 9 | 3.75 mg/ml* | 14 | 0 |
| 10 | 0.37 mg/ml* | 31 | 4 |
| Betamethasone dipropionate | 0.37 mg/ml* | 63 | 17 |
|  | 3.75 mg/ml* | 88 | 25 |
|  | 7.5 mg/ml* | 97 | 38 |
|  | 300 μg/mouse |  |  |

*10 μl was applied to each ear.

The following compounds 2 and 3 were tested in vivo as above.

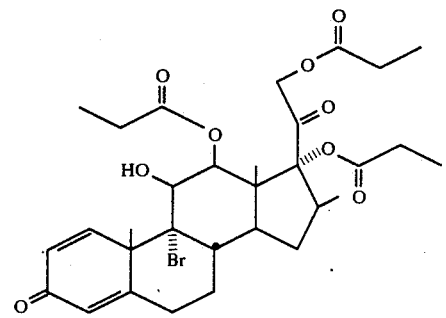

2

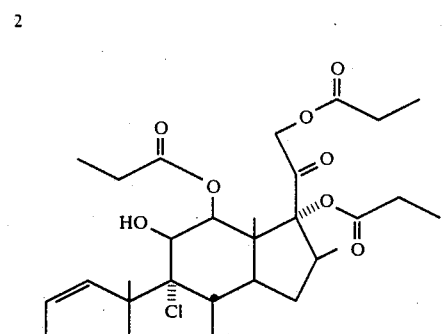

3

The compounds were tested for topical and systemic potency as well as for an evaluation of thymolytic and adrenal suppression effects. As may be seen in Table 2, systemic activity was virtually nonexistent for the compounds of the present invention, while a high topical activity was nevertheless maintained. This is in contrast to Betamethasone dipropionate, used as a control, which showed a high systemic activity. The inventive compounds substantially reduce adrenal suppression and decrease the negative thymolytic effect.

TABLE 2

| Corticosteroids | Dose (μg/mouse) | Anti-inflammatory Potency After One Single Application[a] | | Systemic Effect After Multiple Applications[b] | |
|---|---|---|---|---|---|
| | | Topical | Systemic | Thymolytic Effect[c] | Adrenal Suppression Effect[d] |
| Betametasone dipropionate | 2.5 | 20% | 4% | 10% | 31% |
| Betamethasone dipropionate | 25 | 37% | 10% | 37% | 68% |
| Betamethasone dipropionate | 75 | 65% | 38% | 45% | 76% |
| 2 | 50 | 32% | 0% | 7% | 7% |
| " | 100 | 46% | 0% | 7% | 0% |
| " | 200 | 72% | 0% | 1% | 10% |
| 3 | 50 | 28% | 0% | 8% | 23% |
| " | 100 | 55% | 0% | 0% | 0% |
| " | 200 | 74% | 0% | 0% | 10% |

[a]One single topical application; mice were killed 5 hr later.
[b]One single topical application daily for 5 consecutive days; mice were killed 5 hr after the last application.
[c]The effect was measured by weight loss of the thymus.
[d]The effect was determined by measuring the decrease (inhibition) of increased plasma conticosterone level induced by stress.

What is claimed is:

1. A topical anti-inflammatory pharmaceutical composition comprising an effective inflamation treating amount of a 12-beta substituted glucocorticoid wherein said substituent is selected from the group consisting of hydroxyl and a hydroxyl with an attached lipophilic group in a pharmaceutically acceptable topical carrier.

2. The composition of claim 1 wherein the 12-substituent is a hydroxy.

3. The composition of claim 1 wherein the 12-substituent is a lipophilic group attached to a 12-Beta hydroxy, said lipophilic group selected from an alkyl or aryl-substituted ether, an ester, a carbamate and a carbonate.

4. The composition of claim 1 wherein the 12-substituent is a lower alkyl.

5. The composition of claim 1 wherein the 12-substituent is a lower carboxylic acid ester of a 12-beta hydroxy.

6. A topical anti-inflammatory pharmaceutical composition comprising an effective inflammation treating amount of a 12-beta substituted glucocorticoid wherein said substituent is a group bridging the 12 and 17 carbon atoms and having the formula

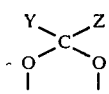

wherein Y and Z represent hydrogen or lower alkyl.

7. A glucocorticoid of the structure

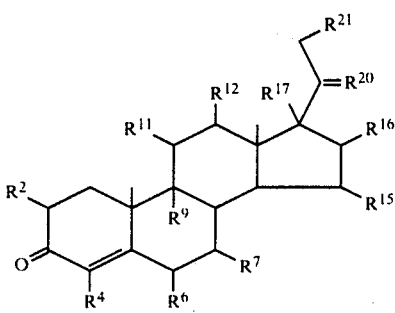

wherein
$R^2$ is hydrogen, a lower alkyl or forms a double bond between the 1 and 2 carbons;
$R^4$ is hydrogen, a lower alkyl or a halogen;
$R^6$ is hydrogen, a lower alkyl, a halogen or it can be one leg of a group bridging the 6 and 7 carbons;
$R^7$ is hydrogen, a lower alkyl, a halogen, a thio compound or it can be one leg of a group bridging the 6 and 7 carbons;
$R^9$ is an alpha group selected from hydrogen and halo;
$R^{11}$ is carboxyl, hydroxyl, or hydrogen;
$R^{12}$ is a beta hydroxyl, beta alkyl, a lower carboxylic acid ester of a beta hydroxyl or a group bridging the 12 and 17 carbon atoms having the formula

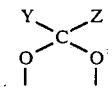

wherein
Y and Z represent hydrogen or lower alkyl;
$R^{15}$ is hydrogen a lower alkyl or a halogen;
$R^{16}$ is hydrogen, an alpha hydroxyl, a lower alkyl, a halogen or is an acetonide or acetal group bridging the 16 and 17 carbons;
$R^{17}$ is hydrogen, a lower alkyl, a halogen or an acetonide or acetal group bridging the 16 and 17 carbons;
$R^{20}$ is a carbonyl, a hydrogen plus a hydroxyl, two hydrogens or a hydrogen plus ketalized hydroxyl; and
$R^{21}$ is a hydroxyl, hydrogen, lower alkyl or a halo.

8. A topical anti-inflammatory pharmaceutical composition comprising an effective anti-inflammatory amount of the glucocorticoid of claim 7 in a pharmaceutically acceptable topical carrier.

9. A glucocorticoid of the structure

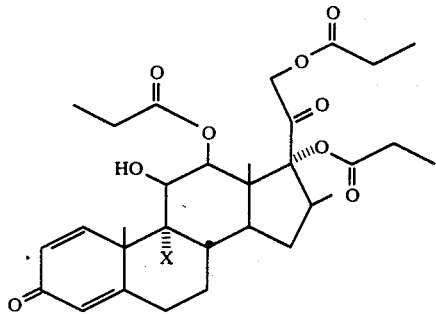

wherein X is fluoro, bromo or chloro.

10. A topical anti-inflammatory pharmaceutical comprising an effective anti-inflammatory amount of the glucocorticoid of claim 9 in a pharmaceutically acceptable topical carrier.

11. A glucocorticoid of the structure

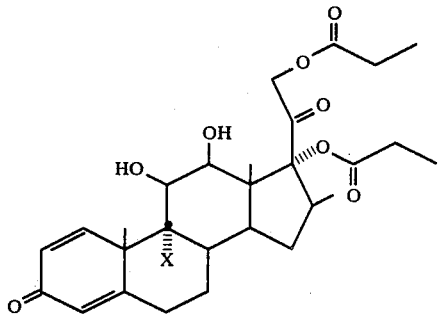

wherein X is fluoro, chloro or bromo.

12. A topical anti-inflammatory pharmaceutical composition comprising an effective anti-inflammatory amount of the glucocorticoid of claim 11 in a pharmaceutically acceptable topical carrier.

13. A glucocorticoid of the structure

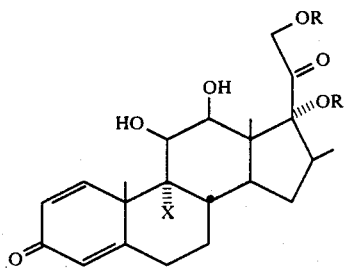

wherein R is hydrogen and X is fluoro, chloro or bromo.

14. A topical anti-inflammatory pharmaceutical composition comprising an effective anti-inflammatory amount of the glucocorticoid of claim 13 in a pharmaceutically acceptable topical carrier.

* * * * *